(12) United States Patent
Abraham-Fuchs et al.

(10) Patent No.: US 7,727,269 B2
(45) Date of Patent: Jun. 1, 2010

(54) DEVICE FOR INTRODUCING A STENT INTO A HOLLOW ORGAN

(75) Inventors: Klaus Abraham-Fuchs, Erlangen (DE); Friedrich Fuchs, Roettenbach (DE); Rainer Kuth, Herzogenaurach (DE); Johannes Reinschke, Nuremberg (DE); Guenter Ries, Erlangen (DE); Rudolf Roeckelein, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1498 days.

(21) Appl. No.: 11/064,858

(22) Filed: Feb. 25, 2005

(65) Prior Publication Data

US 2005/0192660 A1 Sep. 1, 2005

(30) Foreign Application Priority Data

Feb. 26, 2004 (DE) .................. 10 2004 009 237

(51) Int. Cl.
*A61F 2/06* (2006.01)
(52) U.S. Cl. .................. 623/1.11; 600/101; 600/129
(58) Field of Classification Search .......... 600/178, 600/104, 116, 101, 129; 623/1.11
See application file for complete search history.

(56) References Cited

U.S. PATENT DOCUMENTS

| | | | | |
|---|---|---|---|---|
| 5,827,322 A | * | 10/1998 | Williams | 623/1.18 |
| 6,069,420 A | * | 5/2000 | Mizzi et al. | 310/40 MM |
| 6,302,917 B1 | | 10/2001 | Dua et al. | |
| 6,576,005 B1 | * | 6/2003 | Geitz | 623/1.11 |
| 2002/0120182 A1 | | 8/2002 | Muessig et al. | |
| 2002/0161427 A1 | * | 10/2002 | Rabkin et al. | 623/1.11 |
| 2003/0060702 A1 | * | 3/2003 | Kuth et al. | 600/424 |
| 2003/0163177 A1 | * | 8/2003 | Eggers et al. | 607/96 |
| 2005/0209682 A1 | * | 9/2005 | Abraham-Fuchs et al. | 623/1.15 |

FOREIGN PATENT DOCUMENTS

| | | |
|---|---|---|
| DE | 101 42 253 C1 | 4/2003 |
| DE | 699 13 163 T2 | 9/2004 |
| EP | 1 230 892 A1 | 8/2002 |
| WO | WO 00/60996 A1 | 10/2000 |

OTHER PUBLICATIONS

German Office Action issued on Nov. 2, 2004 in German Application No. 10 2004 009 237.0

* cited by examiner

*Primary Examiner*—Brian Casler
*Assistant Examiner*—Elmer Chao
(74) *Attorney, Agent, or Firm*—Harness, Dickey & Pierce, P.L.C.

(57) ABSTRACT

A device is for introducing a stent into a hollow organ, in particular into the gastrointestinal tract of the body of a patient. The device includes a magnet system which covers the area of treatment of the patient and generates a 3D gradient field for remote-controlled movement and orientation of an endorobot. The endorobot is provided with a linear magnet and is freely movable in the hollow organ. Further, the stent, which can be uncoupled from the outside, is secured to the endorobot in a folded-down state so that it can be brought to the site of use and can there be opened out so as to bear firmly on the wall of the hollow organ.

27 Claims, 1 Drawing Sheet

DEVICE FOR INTRODUCING A STENT INTO A HOLLOW ORGAN

The present application hereby claims priority under 35 U.S.C. §119 on German patent application numbers DE 10 2004 009 237.0 filed Feb. 26, 2004, the entire contents of which is hereby incorporated herein by reference.

FIELD OF THE INVENTION

The invention generally relates to a device for introducing a stent into a hollow organ, in particular into the gastrointestinal tract of the body of a patient (human or animal).

BACKGROUND OF THE INVENTION

Diseases in the area of the gastrointestinal tract often lead to narrowing (stenosis). The main causes are inflammations of the intestinal mucosa (Crohn's disease), but also space-occupying tumors which may be benign or malignant. The small intestine of humans is up to 11 meters long. Thus, diagnosis by conventional endoscopic techniques is not possible, or is possible only with a great many limitations. Endoscopic biopsy or even treatment of lesions of the small intestine is therefore not possible. A large part of the small intestine except for the upper jejunum and the terminal ileum is therefore not accessible from outside for introduction of a stent.

When fitting a stent in place with an endoscope, there is also a risk of damaging or even perforating the wall of the intestine. Moreover, an endoscopy procedure is very uncomfortable for the patient and in many cases is possible only under anesthesia, which involves a great deal of input in terms of personnel and technology and thus entails correspondingly high costs.

SUMMARY OF THE INVENTION

It is an object of an embodiment of the invention to make available a device for introducing a stent into a hollow organ of the body of a patient, in particular into the gastrointestinal tract, but also into other gas-filled or fluid-filled cavities of the human or animal body. The device of an embodiment, while avoiding at least one of the disadvantages of the previous techniques, allows a stent to be fitted in place at any desired position in the hollow tract, for example at any desired position in the small intestine.

According to an embodiment of the invention, an object may be achieved by provision of a device which includes a magnet system which covers the area of treatment of the patient and generates a 3D gradient field for remote-controlled movement and orientation of an endorobot which is provided with a linear magnet and is freely movable in the hollow organ and to which the stent, which can be uncoupled from the outside, is preferably secured in a folded-down state so that it can be brought to the site of use and can there be opened out so as to bear firmly on the wall of the hollow organ.

Via the device according to an embodiment of the invention, and with the aid of an endorobot such as the one described for example in DE 101 42 253 C1, the entire contents of which are incorporated herein by reference, it is very easy to bring a stent in a folded-up state or other state of reduced diameter to the desired site of use in a hollow organ, in particular in the small intestine of a patient, by the folded-up stent simply being coupled to the endorobot and being pulled by the latter to the site of use. At the site of use, the stent is then uncoupled and also opened out so that, with its increased diameter, it bears against the inside wall of the hollow organ. With very high magnetic fields, and thus substantial tensile forces of the endorobot, it may be possible to transport the stent without its having to be folded.

Although the bearing action against the inside wall and the resulting greater or lesser friction in any case already provides for retention of the opened-out stent separated from the endorobot, so that the magnetic field for further movement of the endorobot (in particular for its return) cannot displace the stent, it is nevertheless expedient, in a further development of an embodiment of the invention, if the stent is at least substantially non-magnetic and thus cannot be affected by the magnetic field used to move the endorobot.

A wide variety of techniques can be used for opening out the stent. For example, the stent can be folded up resiliently, and the fixing connection keeping it in this folded-up state can be released from the outside. Another possibility would be for the stent to be made of a shape-memory material and for it to be opened out by heating it above the transition temperature. The heating in this case can preferably be effected by a current pulse which can be supplied via the coupling to the endorobot or can be fed in inductively from the outside.

According to a further feature of an embodiment of the present invention, the stent can be made of a material, or coated with a material, which is particularly biocompatible. In addition, it can also be coated with a medicament which preferably dissolves very slowly (depot effect) and permits localized drug therapy, for example delivery of cortisone or of other anti-inflammatory active substances in Crohn's disease.

Field generation of this type for producing a 3D gradient field is known from MR technology. The endorobot contains a bar magnet or a controllable and approximately linear coil so that, by interaction with the gradient field, a linear force and a torque can be generated as long as bar magnet and gradient field are not co-linear. The slope of the gradient determines not just the torque, but also the translation force in magnet axis or coil axis.

It has proven particularly expedient for the magnet system to include a static basic field for compensation of the gravitational force acting on the endorobot, preferably using a superconducting basic field magnet, particularly one composed of a high-temperature superconductor. This compensation of the gravitation acting on the endorobot makes it possible to move the latter such that it floats freely in the corresponding channel of the body (intestine, blood vessel or the like), so that it can neither come stuck nor be damaged by any of the instruments or tools in the body.

It has proven particularly expedient if the static basic field can be controlled so as to compensate for weight changes of the endorobot when loaded and unloaded. Such loading and unloading can, for example, occur when delivering medicaments, said medicaments being able to be released, with the aid of the endorobot according to the invention, specifically at the target sites, for example tumors.

Since the homogeneity volume of the magnet system is in most cases very small, compensation can be obtained, in a further embodiment of the invention, by the patient and the magnet system being movable relative to one another, in particular by the patient being placed on a support table which is adjustable within the magnet system. In this way, as the endorobot continues its movement through the body, it is possible, by shifting the patient, to ensure that the respective position of the endorobot lies as far as possible in the middle of the homogeneity volume.

The endorobot may be advantageously navigated via a force input unit, e.g. a so-called 6D mouse. The gradient direction corresponding to the superposition of the three individual systems can be determined by forward/rearward and right/left tilting and by pressing or lifting, and the amplitude can be determined by turning the input lever. It is advantageous if the forces acting on the input unit correspond to or are proportional to the force acting on the instrument.

In one embodiment of the invention, provision can also be made for the endorobot to have a lighting device for illuminating its surroundings. When using infrared LEDs, this lighting device can be very bright but in this case permits only black and white reception with the aid of a video camera which is preferably also built into the endorobot. To receive color images too, it is possible to use high-power LEDs in three colors or micro fluorescent lamps, although these have the disadvantage of high ignition voltages.

The images from the aforementioned video camera are to be sent by wireless transmission from inside the body to a monitor, and the video camera is advantageously equipped with a device/method allowing the image to be turned about the central axis.

According to another advantageous feature of an embodiment of the invention, the endorobot can be provided with a locating device/method, working particularly by transponder, which allows the position to be presented on a screen showing the anatomical environment. The anatomical environment can in this case be presented in sectional images, for example, as is known in commercial navigation systems.

The endorobot advantageously has a helicopter mode which is characterized by the fact that the gradient field is controlled via detection by the transponder so that the endorobot remains stationary or can be moved linearly along a predetermined distance.

An in-built accumulator which is used to power the endorobot and can be recharged via an external alternating field can be advantageously provided.

BRIEF DESCRIPTION OF THE DRAWINGS

Further advantages, features and details of the invention will become clear from the following description of an illustrative embodiment given with reference to the drawings, in which.

DETAILED DESCRIPTION OF THE EXEMPLARY EMBODIMENTS

Figure 2:
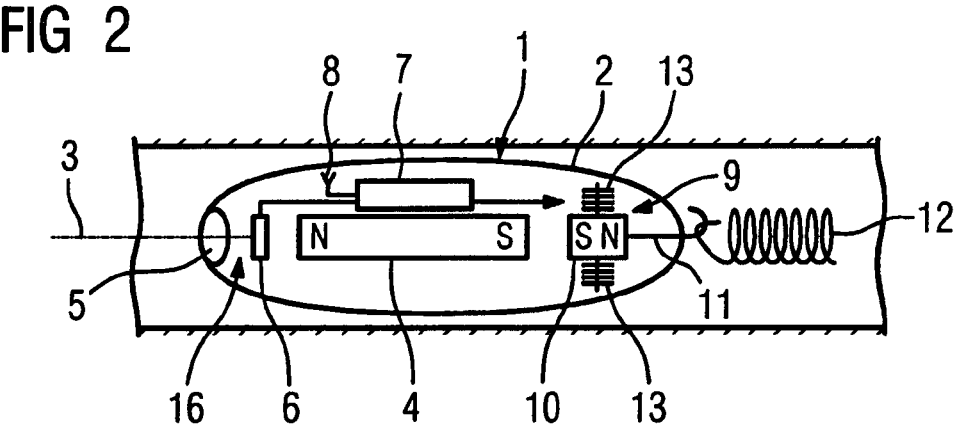
FIG. 2 shows a schematic representation of the structure of the endorobot with attached, folded-up stent.
Figure 3:
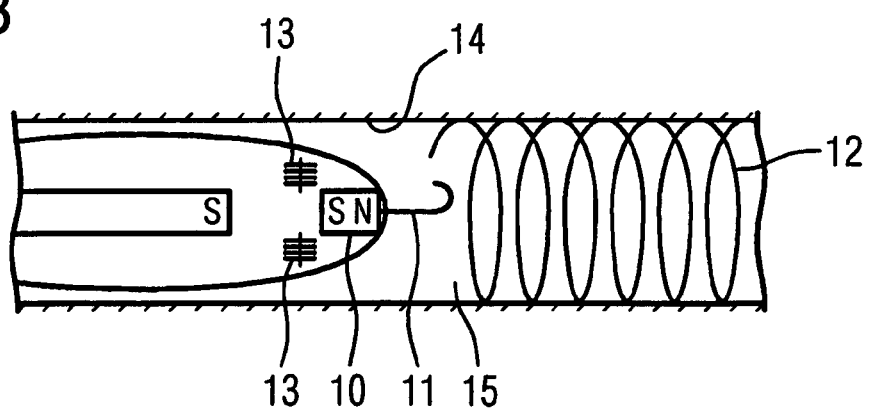
FIG. 3 shows a partial view of the endorobot according to FIG. 2 after release of the coupling between endorobot and stent and after subsequent opening-out of the stent, so that it is braced in the hollow organ at the desired position.

The endorobot 1 shown in FIGS. 2 and 3 has an elongated, for example ellipsoid housing 2 in which a bar magnet 4 is arranged in line with the longitudinal axis 3. A video camera 16 including a lens 5 and a CD sensor 6 takes pictures which can be transmitted to the outside via an HF transmitter/receiver 7 and antenna 8, and control commands can also be sent to the receiver 7 from outside via the antenna. In this way it is possible, from outside, to issue control commands, for example for a coupling mechanism 9.

In the illustrative embodiment shown according to FIGS. 2 and 3, this coupling mechanism 9 includes a magnet 10 which is provided with a hook 11 for attachment of the small folded-up stent 12. By use of a current pulse acting on the piezo stack 13, the locking of the small holding magnet is opened, the coupling travels outward and the connection to the stent is released. The stent then opens in the axial direction and also radially outward so that the stent, as is shown in FIG. 3, bears with pre-stressing against the wall 14 of the hollow organ 15, for example the small intestine of a patient.

Figure 1:
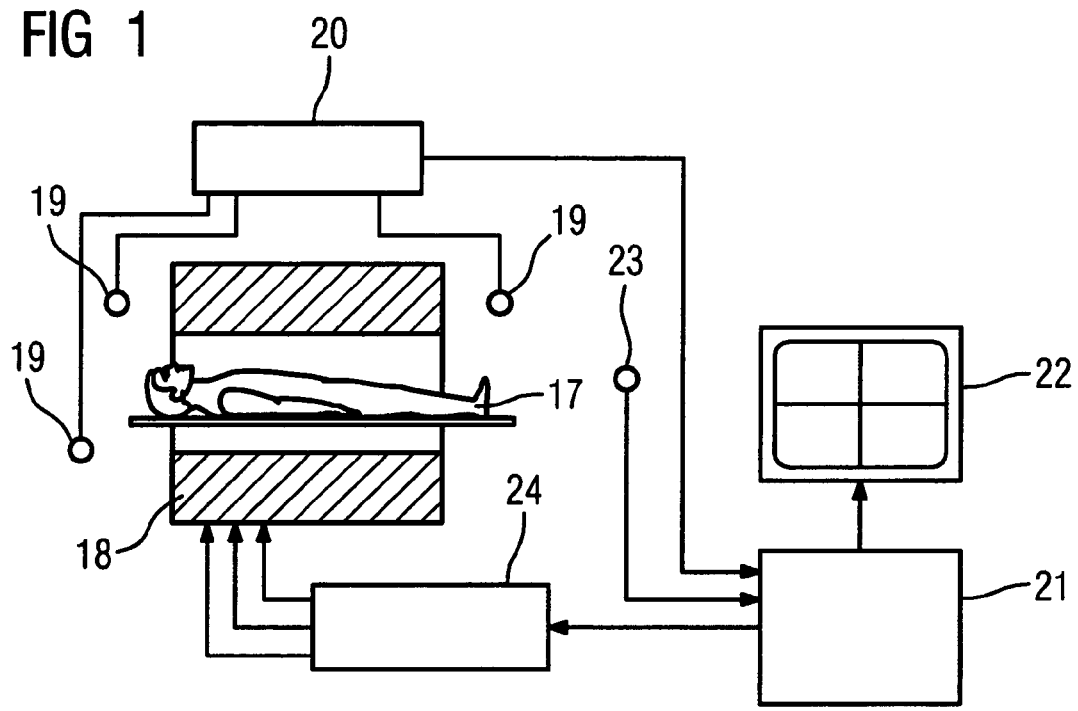
FIG. 1 shows a schematic representation of the device for controlling the endorobot transporting the stent in the body.

Referring to FIG. 1, this shows the way in which an endorobot according to an embodiment of the invention is controlled in an installation. The patient 17 lies in a gradient coil 18 shown here only in cross section and known from commercial MR scanners. The area of the body to be examined, that is to say the area in which the endorobot according to FIGS. 2 and 3 is intended to move, is situated within the linearity volume of the gradient coil 18. Antennas 19 receive signals from the transponder or transponders and forward them to the position-locating device 20. The latter forwards the 3D location to the central computer 21 cyclically or upon changes from previous values, and the central computer 21 presents, on the monitor 22, sectional images of a 3D data set in axial, coronal and sagittal plane, respectively.

By use of a further antenna 23, images from the video camera are received by wireless transmission and are likewise presented on the monitor 22. Reference number 24 designates a three-channel gradient amplifier for controlling the gradient coils via the central computer 21. The figure does not show the nature of the input device, preferably designed as 6D mouse, nor the basic field magnet for compensation of the gravitational effect on the endorobot.

The endorobot 1 is preferably designed in such a way that it can be sterilized, and in this case different sterilization procedures can be employed depending on the kind of structure and on the possibility of securely sealing the inside of the endorobot. Optimal autoclaving at 132° C. and a pressure of several bar is in most cases not feasible in the presence of several internal cavities, especially when there are also still external seals. In the case of a water-tight housing, non-pressurized cleaning could be performed, but also plasma sterilization or cold-gas sterilization.

The invention is not limited to the illustrative embodiment shown. In addition to another design of the endorobot and of the system for controlling it in a patient's body, the stent could of course also be folded up and opened out in some other way, and another kind of coupling to the endorobot could also be provided.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for introducing a stent into a hollow organ, comprising:

an endorobot including a linear magnet, the endorobot adapted to be freely movable in the hollow organ, wherein a stent, uncoupleable from the outside, is secured to the endorobot in a folded-down state and, at a site of use, is adapted to be opened so as to bear firmly on a wall of the hollow organ;

a magnet system which covers an area of treatment of a patient and generates a 3D gradient field for remote-controlled movement and orientation of the endorobot; and a coupling mechanism within the endorobot, the coupling mechanism being configured to release the stent secured to the endorobot, wherein the coupling mechanism includes a coupling magnet and a piezo-stack, the coupling mechanism being connected to a hook configured to hold the stent and the coupling mechanism is configured to release the stent upon receipt of a current pulse acting on the piezo-stack.

2. The device as claimed in claim 1, wherein the stent is at least substantially non-magnetic.

3. The device as claimed in claim 1, wherein the endorobot contains a bar magnet.

4. The device as claimed in claim 1, wherein the endorobot contains a controllable and at least approximately linear coil.

5. The device as claimed in claim 1, wherein the magnet system includes a static basic field for compensation of a gravitational force acting on the endorobot.

6. The device as claimed in claim 1, wherein the magnet system includes a superconducting basic field magnet.

7. The device as claimed in claim 5, wherein the static basic field is controllable so as to compensate for weight changes of the endorobot when loaded and unloaded.

8. The device as claimed in claim 1, wherein the patient and the magnet system are movable relative to one another.

9. The device as claimed in claim 1, further comprising a support table configured to receive a patient, the support table being adjustable within the magnet system.

10. The device as claimed in claim 1, wherein the endorobot includes a lighting device for illuminating its surroundings.

11. The device as claimed in claim 1, wherein the endorobot is equipped with a video camera.

12. The device as claimed in claim 1, wherein the endorobot includes locating means for allowing the position to be presented on a screen showing an anatomical environment.

13. The device as claimed in claim 1, wherein an in-built accumulator is used to power the endorobot and is rechargeable via an external alternating field.

14. The device as claimed in claim 1, wherein the endorobot includes a helicopter mode in which, by regulation of the gradient field via detection by the transponder, it remains stationary or is moved a predetermined distance.

15. The device as claimed in claim 1, further comprising an input unit configured to control the endorobot in such a way that forces acting on the input unit correspond to or are proportional to forces acting on the endorobot.

16. The device as claimed in claim 1, wherein the endorobot is configured to be controllable via a 6D mouse.

17. The device as claimed in claim 1, wherein the stent is adapted to be folded up resiliently, and the fixing connection is releasable from outside.

18. The device as claimed in claim 1, wherein the stent comprises a shape-memory material and is heated above the transition temperature in order to open out.

19. The device as claimed in claim 18, wherein the heating is effected by way of a current pulse which is at least one of supplied via the coupling to the endorobot and fed in inductively from outside.

20. The device as claimed in claim 1, wherein the stent is at least one of made of a material, and coated with a material.

21. The device as claimed in claim 1, wherein the stent is coated with a medicament.

22. The device as claimed in claim 1, wherein the device is configured to introduce the stent into a gastrointestinal tract of a patient.

23. The device as claimed in claim 1, wherein the magnet system includes a superconducting basic field magnet, composed of a high-temperature superconductor.

24. The device as claimed in claim 20, wherein the material is biocompatible.

25. The device as claimed in claim 21, wherein the medicament is one that dissolves slowly.

26. A device for introducing a stent into a hollow organ, comprising:
an endorobot including a linear magnet and adapted to be movable in the hollow organ, wherein a stent, uncoupleable from the outside, is adapted to be secured to the endorobot in a folded-down state and is adapted to be opened so as to bear firmly on a wall of the hollow organ;
a magnet system, adapted to at least partially cover an area of treatment of a patient and adapted to generate a field for remote-controlled movement and orientation of the endorobot; and
a coupling mechanism within the endorobot, the coupling mechanism being configured to release the stent secured to the endorobot, wherein the coupling mechanism includes a coupling magnet and a piezo-stack, the coupling mechanism being connected to a hook configured to hold the stent and the coupling mechanism is configured to release the stent upon receipt of a current pulse acting on the piezo-stack.

27. The device as claimed in claim 26, wherein the stent is at least substantially non-magnetic.

* * * * *